(12) United States Patent  
Lawrence

(10) Patent No.: US 7,237,811 B1
(45) Date of Patent: Jul. 3, 2007

(54) CASEMENT WINDOW LATCH ASSEMBLY

(76) Inventor: Barry G. Lawrence, 1515 Johnstown Rd., Thomasville, NC (US) 27360

( * ) Notice: Subject to any disclaimer, the term of this patent is extended or adjusted under 35 U.S.C. 154(b) by 134 days.

(21) Appl. No.: 11/110,172

(22) Filed: Apr. 20, 2005

(51) Int. Cl.
*E05C 1/06* (2006.01)

(52) U.S. Cl. .................. 292/39; 292/172; 292/302; 49/394

(58) Field of Classification Search ............ 292/39, 292/33, 300, 302, 142, 160, 172, 341.15; 49/394, 395
See application file for complete search history.

(56) References Cited

U.S. PATENT DOCUMENTS

| | | | | |
|---|---|---|---|---|
| 1,131,247 | A * | 3/1915 | Kiekert | 292/51 |
| 3,478,919 | A * | 11/1969 | Turpen | 220/324 |
| 5,139,291 | A | 8/1992 | Schultz | 292/42 |
| 5,219,195 | A | 6/1993 | Lawrence | 292/336.3 |
| 5,536,052 | A | 7/1996 | Maier | 292/63 |
| 5,669,180 | A | 9/1997 | Maier | 49/181 |
| 5,669,639 | A | 9/1997 | Lawrence | 292/175 |
| 5,740,632 | A * | 4/1998 | Peterson et al. | 49/460 |
| 5,970,656 | A | 10/1999 | Maier | 49/181 |
| 5,996,283 | A | 12/1999 | Maier | 19/181 |
| 6,068,306 | A | 5/2000 | Brautigam | 292/242 |
| 6,142,541 | A | 11/2000 | Rotondi | 292/241 |
| 6,161,881 | A * | 12/2000 | Babka et al. | 292/26 |
| 6,450,554 | B1 | 9/2002 | Rotondi et al. | 292/158 |
| 6,568,723 | B2 | 5/2003 | Murphy et al. | 292/241 |
| 6,767,038 | B1 | 7/2004 | Huml | 292/158 |
| 6,871,886 | B2 | 3/2005 | Coleman et al. | 292/241 |

OTHER PUBLICATIONS

U.S. Appl. No. 10/867,370, filed Jun. 14, 2004, Lyn O. Trickel.
Photo showing standard window lockbar strip with arrows pointing to lock points thereon (undated).
Photo of enlarged section (side view) of lockbar strip as seen in A1 (undated).
Photo showing operator removed from lockbar strip seen in A1 (undated).

* cited by examiner

*Primary Examiner*—Gary Estremsky

(57) ABSTRACT

A rack and pinion are mounted on a casement window frame to operate a vertically disposed polymeric latch keeper. The moveable rack includes a plurality of teeth which are engageable with latch keepers spaced therealong. The pivotable window section includes latches which are rigidly affixed thereto. Thus when the window is closed a pinion can be rotated and thus drive the rack to engage the latch keepers into mating engagement with the latches for security and wind load resistance. The method of installation utilizes frangible spacers affixed to the latches for quick and easy alignment with the latch keepers.

18 Claims, 6 Drawing Sheets

CASEMENT WINDOW LATCH ASSEMBLY

FIELD OF THE INVENTION

The invention herein pertains to latch assemblies for windows and particularly pertains to a latch assembly for a casement window which employs a moveable rack which operates one or more latch keepers for engagement with fixed latches.

DESCRIPTION OF THE PRIOR ART AND OBJECTIVES OF THE INVENTION

Many homes and other buildings have long used casement windows which pivot from an open to a closed position by the use of a standard hand crank. Various methods and hardware have been used in the past to lock such windows and conventional lock bars are commonly employed. Such lock bars generally include a metal strip having various lock points therealong. As building requirements have increased the wind load minimums in recent years, the number of lock points has increased, such as from two (2) per window to as many as four (4). Such lock bars are generally made from a flat steel strip that is punched or drilled to accept rollers or lock points therealong for attachment to the casement frame. Lock bars are generally purchased in increments in length. Conventional small casement windows are approximately two (2) feet in height whereas larger casement windows are about seven (7) feet in height. A typical window fabricator therefore will have to purchase many different lengths of lock bars to accommodate the different window sizes manufactured. This puts a large burden and financial drain on the typical window fabricator to maintain a sufficient inventory as many window sizes are often specified in each new house built.

Further, building codes vary from state to state and county to county, requiring window manufacturers to maintain a large inventory of lock bars.

It is a further problem in the manufacture of a typical casement window to properly jig and align the latches and keepers. Misalignment as little as one millimeter will often prevent closure and proper locking of the window.

Thus, in view of the problems and disadvantages of conventional casement window locking assemblies, it is an objective of the present invention to provide a casement window latch assembly which is relatively inexpensive to inventory, easy to install and align and simple for the homeowner to operate.

It is yet another objective of the present invention to provide a latch assembly which allows the window manufacturer to vary the components for security and minimum wind load requirements.

It is another objective of the present invention to provide a latch assembly which allows easy installation without requiring a jig for keeper and latch alignment.

It is a further objective of the present invention to provide a latch assembly which includes a durable polymeric rack and pinion.

Various other objectives and advantages of the present invention will become apparent to those skilled in the art as a more detailed description is set forth below.

SUMMARY OF THE INVENTION

The aforesaid and other objectives are realized by providing a latch assembly for casement windows which includes a rack and pinion mounted on the window frame. An arcuate pinion is affixed to a lockable handle. When the handle is lifted the pinion urges the rack downwardly which engages a series of slideable latch keepers positioned therealong. A rotatable pawl on the bottom of the handle engages a notch along the bottom of the pinion cover to lock the handle in a downward or closed posture. A coil spring biases the pawl into locking engagement. Upon disengagement, the handle will first in an upwards direction rotate to operate and direct the rack downwardly to disengage the keepers from the latches. Thereafter, a standard hand crank can be rotated to open the pivotable window section as usual. The method of installing the latch assembly utilizes a thin frangible spacer which is affixed to each latch. The distal end of the spacer is positioned in the keeper housing to align the keeper housing and latch. The keeper housing can then be mounted on the casement frame such as by screws and the latch can be positioned accordingly along the pivotable section of the window. A suitable number of keeper housings and latches can be thusly placed respectively along the window frame and pivotable window section using mounting screws or other standard fasteners. The pivotable window section is then closed into a contiguous relation with the frame, the frangible spacers broken from each latch and the handle rotated downwardly to engage the keepers with the latches for security purposes.

While the examples shown herein are for casement (type) windows the latch assembly disclosed can likewise be used for doors, hatches and otherwise as the term "window" is used herein in the generic sense for adaption to structural openings.

DETAILED DESCRIPTION OF THE PREFERRED EMBODIMENT AND OPERATION OF THE INVENTION

Figure 1:
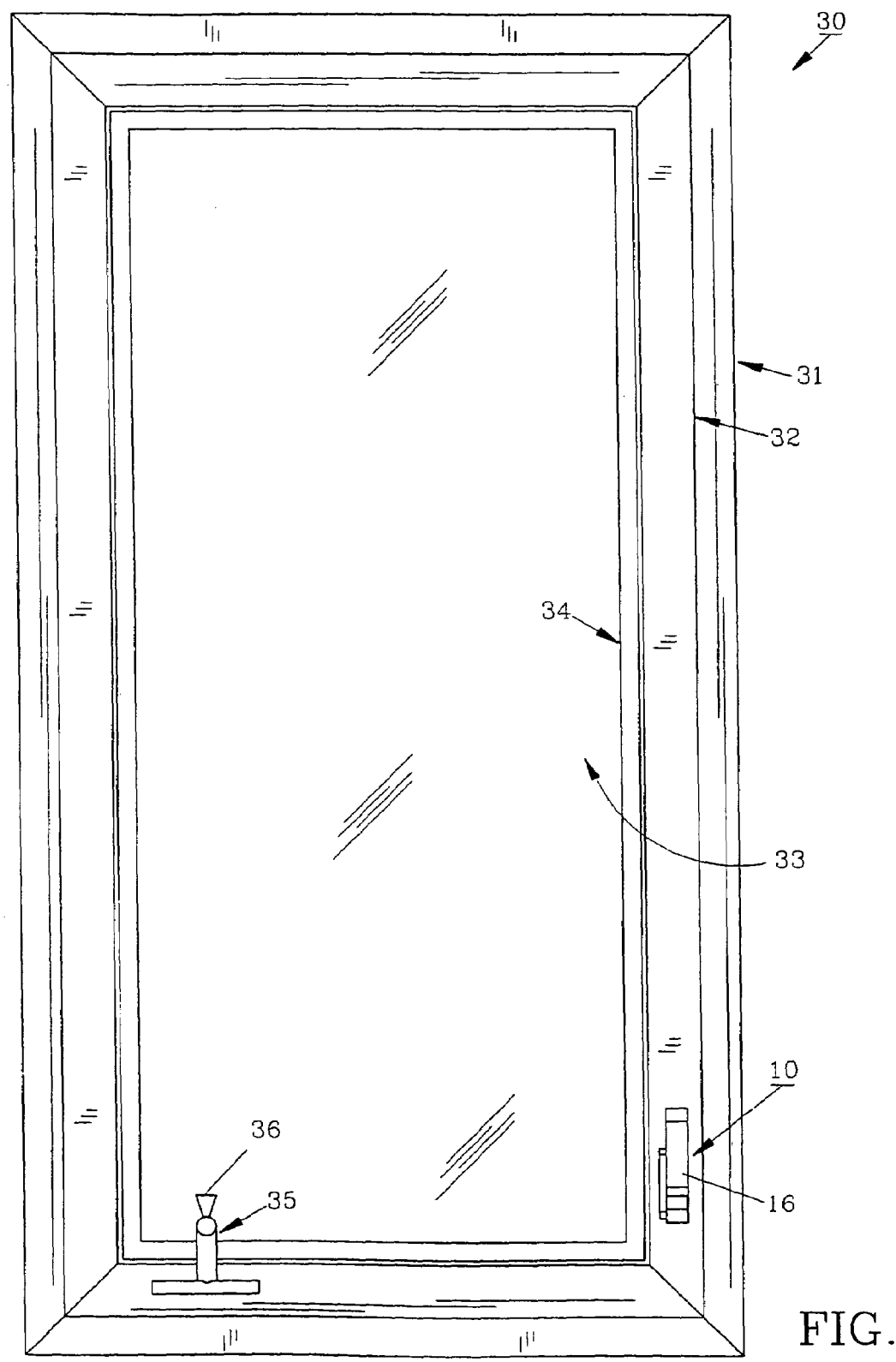
FIG. 1 illustrates a front elevational view of a typical closed casement window with the latch assembly of the invention utilized thereon.
Figure 2:
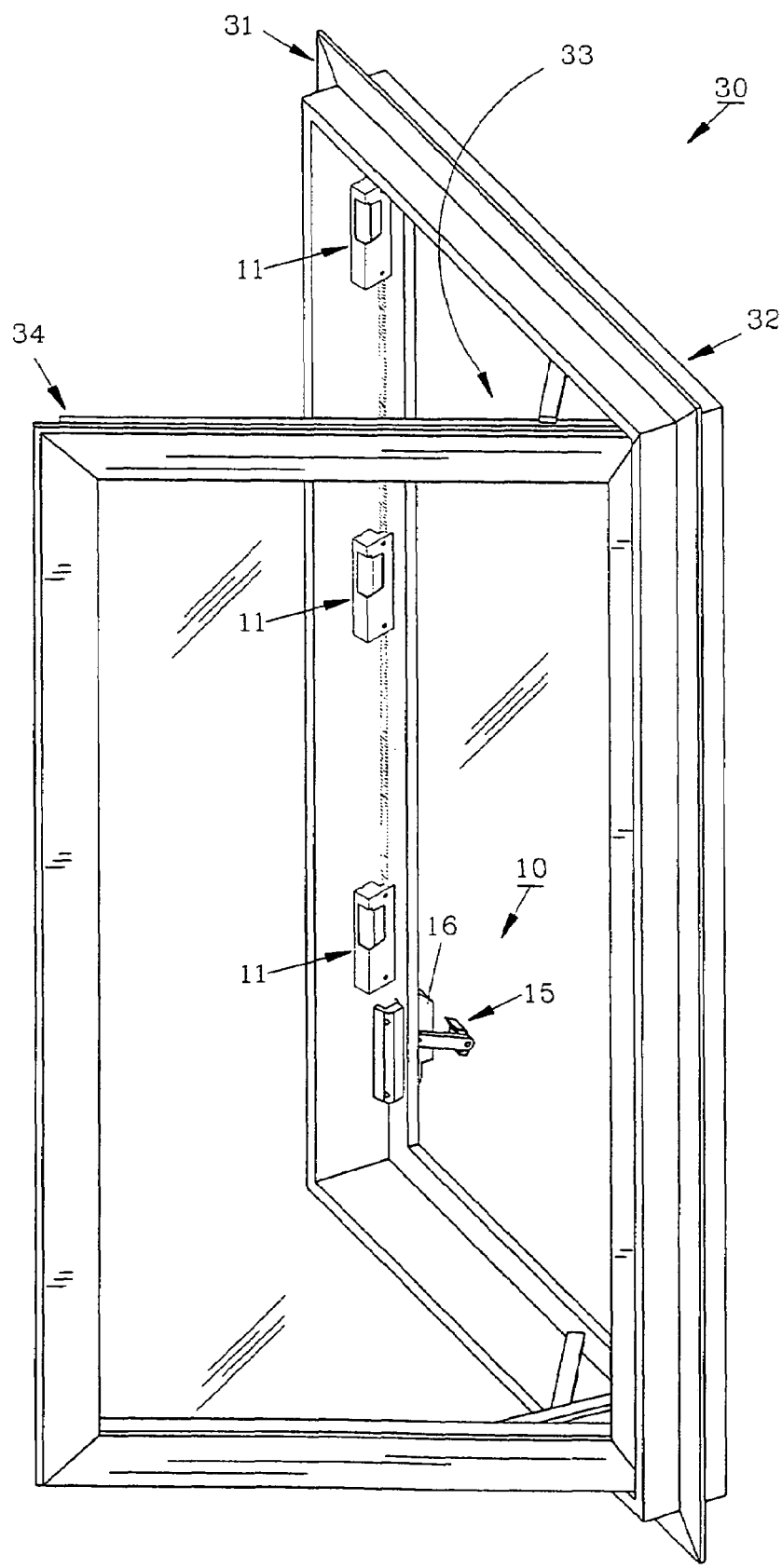
FIG. 2 shows the casement window of FIG. 1 open and in a somewhat rear view from that seen in FIG. 1.
Figure 3:
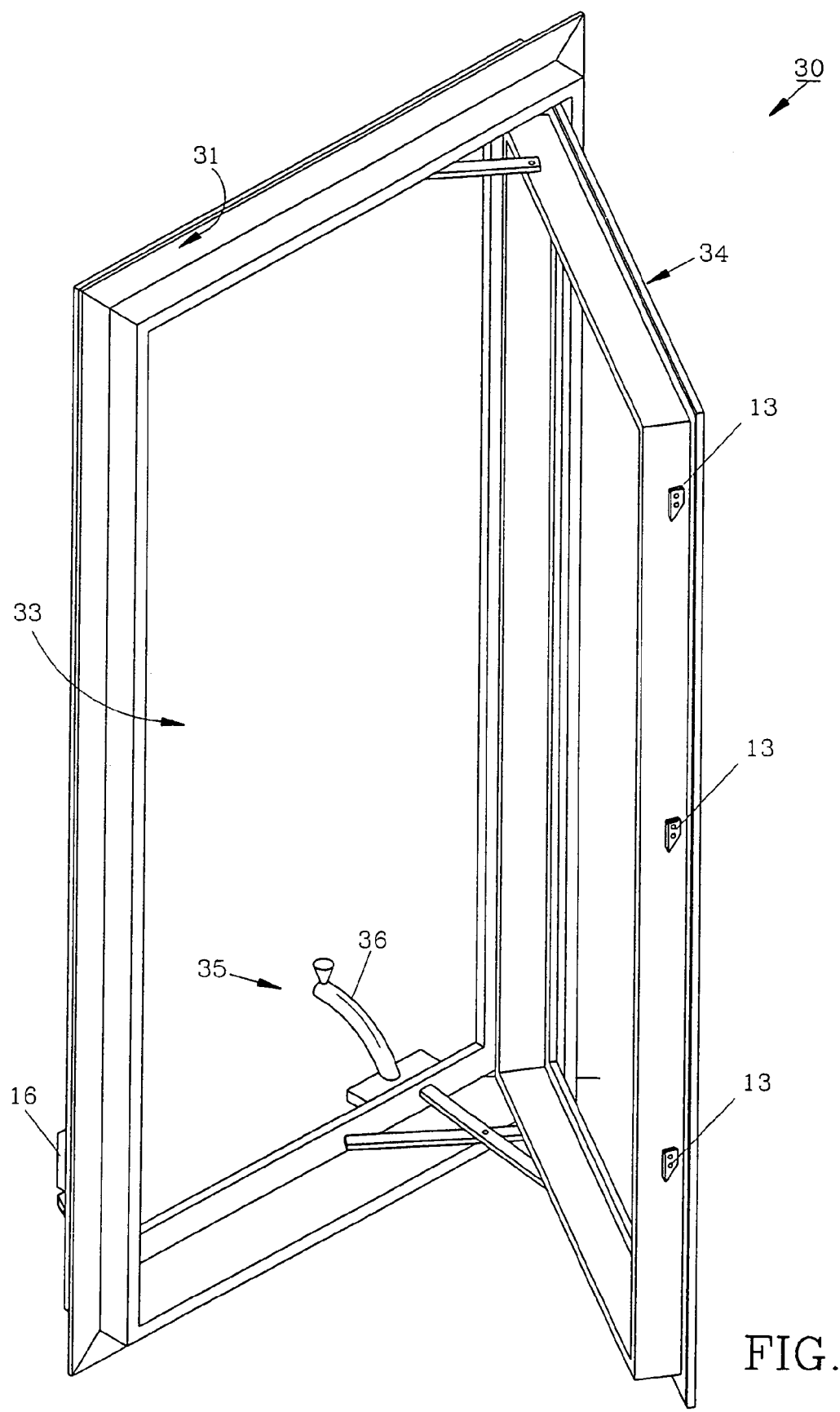
FIG. 3 shows yet another view of the open casement window as seen in FIG. 2.
Figure 4:
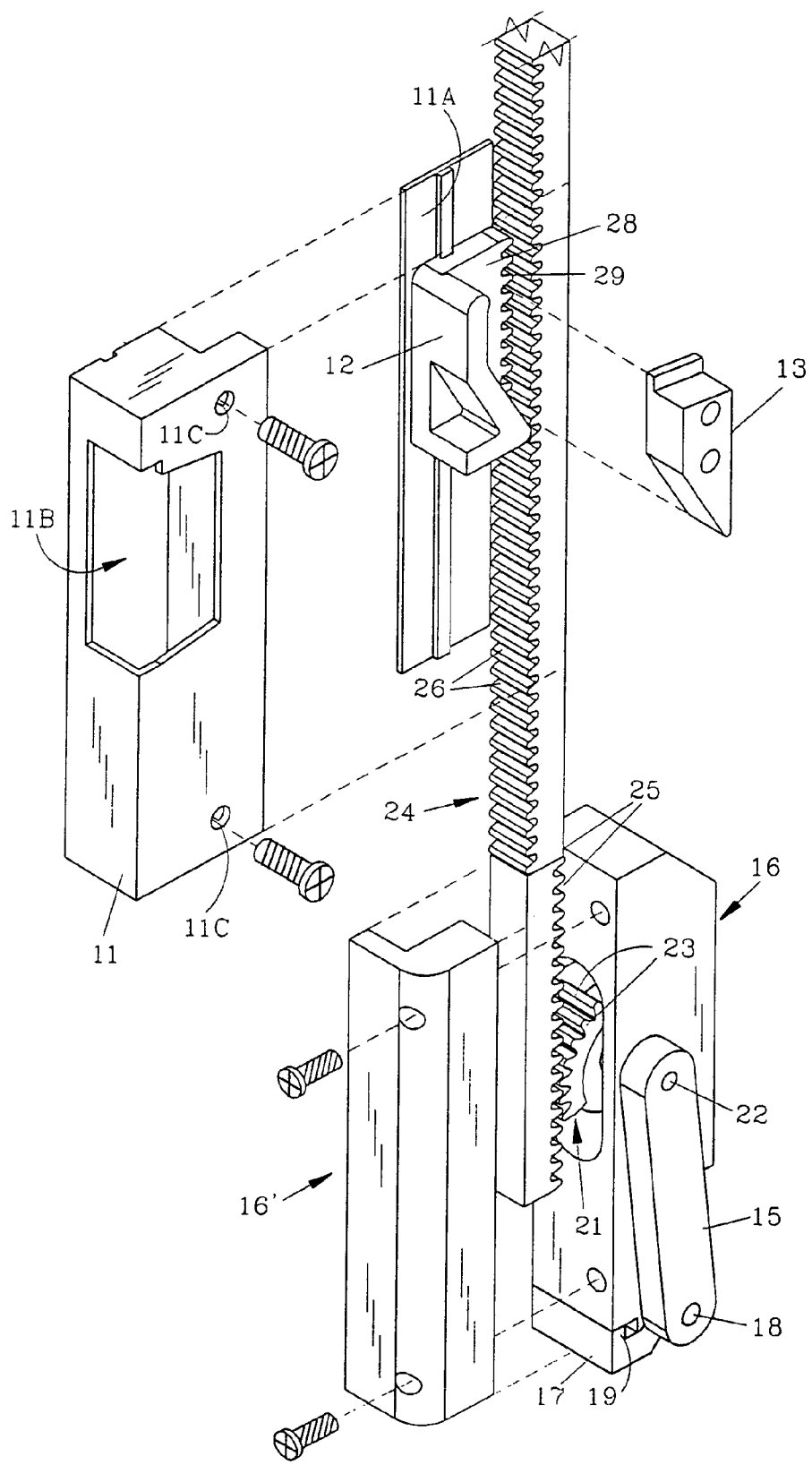
FIG. 4 depicts an enlarged, exploded, fragmented view of the latch assembly of the invention as removed from the window.
Figure 5:
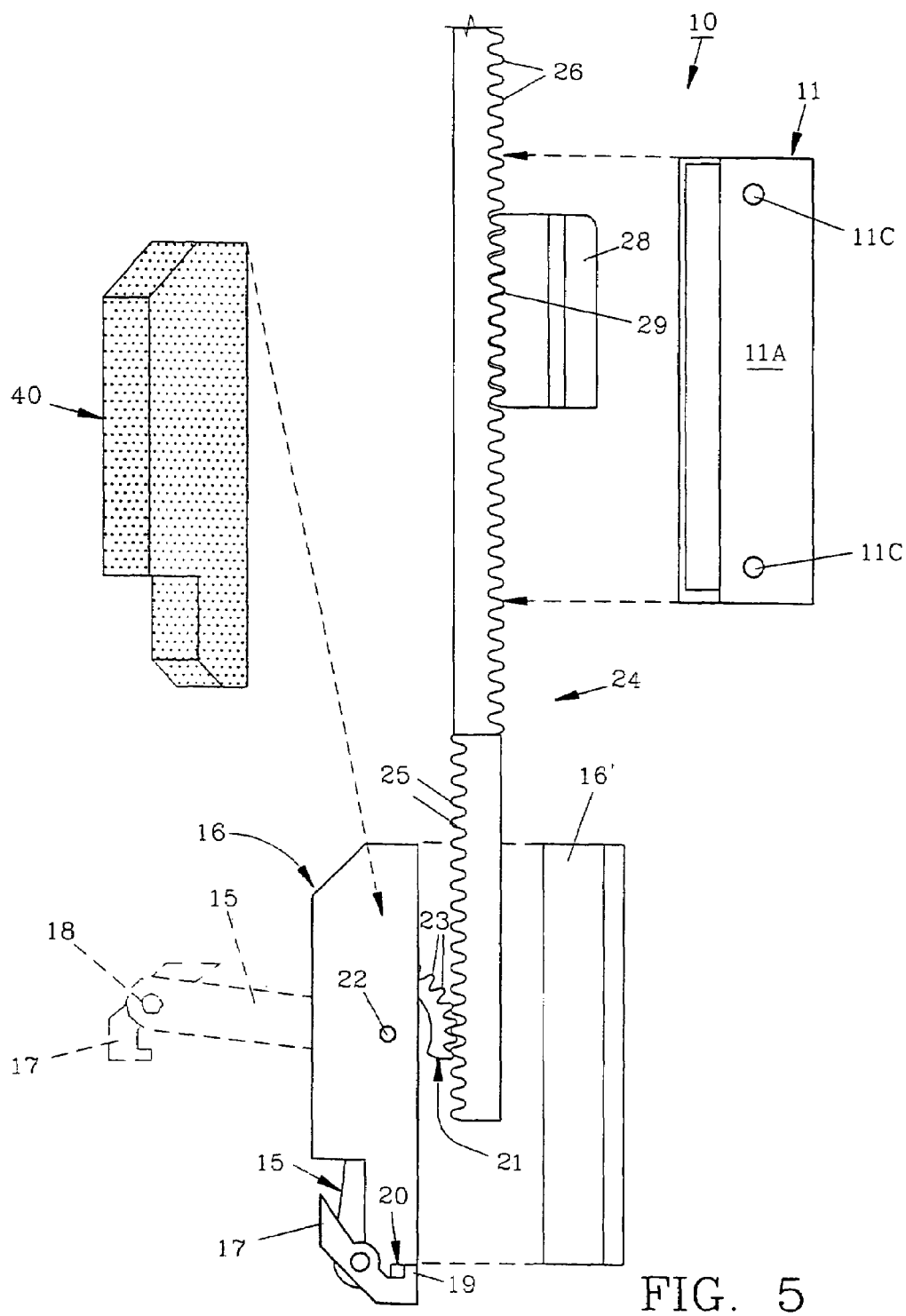
FIG. 5 shows yet another enlarged, exploded, fragmented view of the latch assembly as seen in FIG. 4.

For a better understanding of the invention and its operation, turning now to the drawings, preferred casement window latch assembly 10 is shown fragmented and enlarged in FIGS. 4 and 5 as removed from typical vertical casement window 30 seen in FIGS. 1, 2 and 3. Casement window 30 is shown in a closed front view in FIG. 1 as seen from the inside of a house or other building after installation. Casement window 30 includes vinyl flange 31 used for installing window 30 as would be understood by those skilled in the art. Window 30 further includes standard outer vinyl frame 32 which is rectangular in shape and defines window opening 33 and pivotable rectangular section 34 which is conventionally affixed to frame 32 and operated by standard hardware 35. Pivotable section 34 is shown in FIG. 1 in a closed posture and is seen open in FIGS. 2 and 3. Standard window hardware 35 includes hand crank 36 used to open and close pivotable section 34, hinges (not seen) and conventional upper and lower crank arms. Thus by rotating hand crank 36 pivotable section 34 opens and closes as usual.

Preferred latch assembly 10 maintains pivotable section 34 securely closed within frame 32 and provides a variety of advantages over conventional casement window locking assemblies such as easier installation by relatively unskilled workers, a selection of locking options and the ability to work on a variety of different casement windows.

In FIG. 2 latch assembly 10 includes three (3) keeper housings 11 mounted by conventional screws to the inside of frame 32. Keeper housing 11 is shown enlarged in FIGS. 4 and 5. As would be understood, more or less housings 11 may be employed on casement window 30, depending on the rack length, dimensions and degree of security/wind load minimum desired. Keeper housing 11 is snap fitted to housing base 11A when assembled and contains slideable latch keeper 12 therein. Latch keeper 12 (FIG. 4) has a somewhat L-shape for engagement with latch 13 as seen positioned on the outer edge of pivotable section 34 in FIG. 3. Latch keeper 12 (FIG. 4) includes keeper arm 28 defining teeth 29 thereon as seen in FIG. 4. Latch 13 is preferably formed from a rigid polymeric material such as a polycarbonate or propylene but metals or other durable plastics or materials may likewise be used. Latch 13 is wedge-shaped to complement the rear engagement surfaces of keeper 12 as shown in FIG. 4. Keeper 12 is likewise preferably formed from a rigid polymeric material although metal or other rigid materials may be used if practical.

In further explanation of the components and operation of latch assembly 10 as seen in FIGS. 1 through 5, preferred latch handle 15 is disengaged from pinion cover 16 by rotation of spring loaded pawl 17 around pawl pin 18 seen in FIG. 4. A coil wire spring (not shown) is included on pawl pin 18 designed to maintain pawl 17 in a normally closed position as shown in FIGS. 4 and 5. Notch 20 is defined along the bottom surface of pinion cover 16 as seen in FIGS. 4 and 5 to allow pawl tooth 19 of pawl 17 to thereby engage and lock handle 15 in a closed posture for security. To operate latch assembly 10, pawl 17 is manually rotated by finger pressure in a counter clockwise direction as seen in FIG. 5 to disengage (open) pawl tooth 19 from notch 20 of pinion housing 16. Handle 15 is then lifted and upon lifting, (seen in ghost fashion in FIG. 5) pinion 21 rotates about pinion axle 22 whereby pinion teeth 23 engage front rack teeth 25 to move rack 24 downwardly as desired. Preferred rack 24 as shown in FIG. 4 is made from a durable polymeric material, preferably a polycarbonate, but aluminum or other materials may also be used. Rack 24 is formed from two (2) rack sections joined together to provide front rack teeth 25 and rear rack teeth 26 as seen in FIGS. 4 and 5. Racks as used herein are manufactured in standard eighteen (18) inch (45.72 cm) lengths, but can be made in various other lengths should the combination facilitate a more efficient linkage length. As needed, rack 24 can by cut and/or coupled to a second rack 24 or section thereof by use of adhesives, screws, bolts or other standard fasteners. Other rack embodiments may be made with male and female ends (not seen) to allow the racks to "snap" together for a desired length without additional fasteners. While teeth are used on preferred rack 24, holes, pegs, slots or the like could be used for alternate rack and pinion mechanisms.

Keeper arm teeth 29 within housing 11 engage rack rear teeth 26 for approximately one (1) inch (2.54 cm) as shown in FIG. 5 whereby rotation of handle 15 will cause rack 24 to selectively move upwardly or downwardly as desired, thereby slideably directing keeper 12 into engagement and disengagement with latch 13 when pivotable window section 34 is closed. To open pivotable window section 34, latch keepers 12 are disengaged as described from latches 13 and rotation of hand crank 36 will separate pivotable section 34 from outer frame 32. As would be understood, only one keeper housing 11 is shown in FIGS. 4 and 5 although multiple keeper housings 11 are seen in FIG. 2 and multiple latches 13 are seen in FIG. 3.

Figure 6:
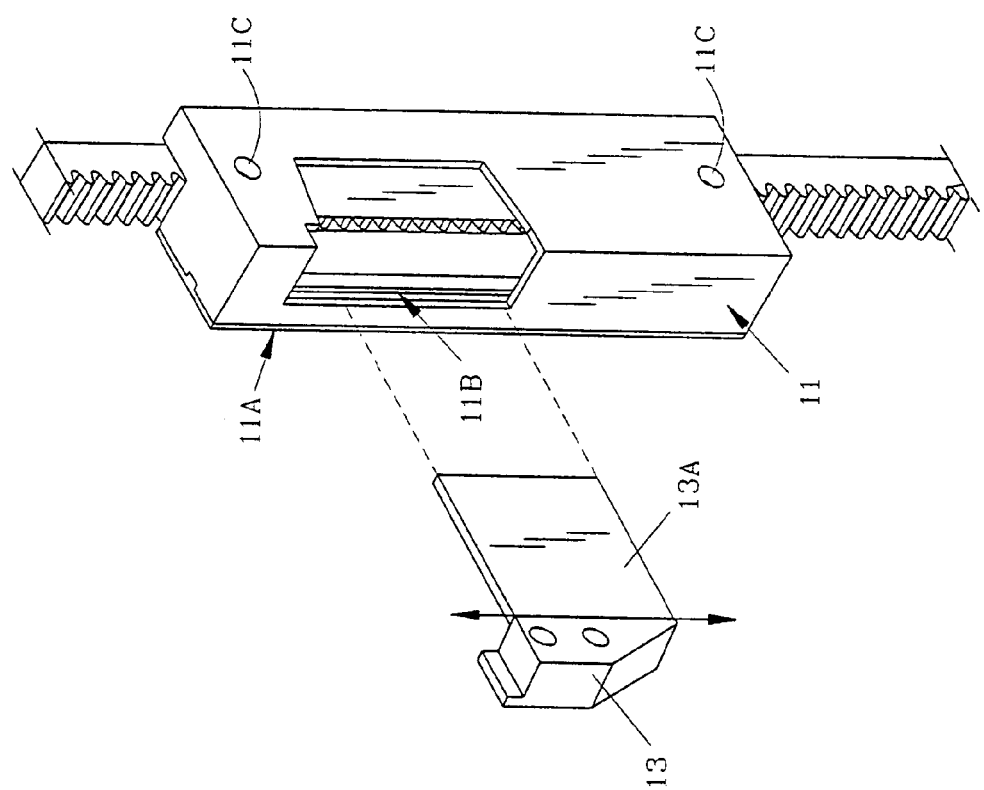
FIG. 6 illustrates a latch as seen in FIG. 4 with the frangible spacer affixed thereto before removal.

The method of use of preferred casement window latch assembly 10 as shown in FIGS. 1, 2 and 3 is as follows. First, a standard casement window is selected having a standard hand crank, pivotable section and the like. Next, handle 15 with pawl 17, pinion cover 16 having pinion cover bracket 16' with arcuate pinion 21 contained therein are affixed by conventional screws (not seen) to the window frame such as frame 32 seen in FIG. 1 by cutting frame section 32 as is usual in the industry. Handle 15 and pinion cover 16 can be manufactured in a variety of designer colors and coatings or materials. A soft or resilient polymeric foam or other coating or shroud 40 (shown slightly turned for clarity in FIG. 5) can be applied as an overmolding to the structural material of pinion cover 16. The design of which would be dependent upon aesthetic and/or functional purposes, so as to have two (2) dissimilar materials, one for structural and the shroud for safety and insulation purposes if desired. The same soft shroud material could also be applied to handle 15 and pawl 17 as desired. Next, rack 24 of sufficient length is selected and assembled as required, depending on the window height and number of keeper housings 11 desired. Two or three keeper housings 11 are generally sufficient although more or less may be employed depending on the exact window height and requirements. Keeper housings 11 are then meshed with rack 24. Latches 13 with spacers 13A (FIG. 6) are inserted into each keeper housing 11 through latch opening 11B. Standard screws (not seen) are then inserted through apertures 11C within each keeper housing 11 and housing base 11A to affix keeper housing 11 to frame 32 at the desired location. Pivotable window section 34 is then closed and latches 13 are aligned horizontally and vertically. Spacers 13A maintain latch 13 in place whereby pivotable section 34 can be slightly opened and latches 13 can be mounted by conventional screws. Once mounted spacers 13A can be removed such as by cutting or manually breaking (along the double headed arrow as seen in FIG. 6) thus the window (or door) is now perfectly aligned so latches 13 will make exact engagement with each keeper housing 11. This method provides much quicker, more precise and more convenient alignment then standard practices which require mounting jigs.

The illustrations and examples provided herein are for explanatory purposes and are not intended to limit the scope of the appended claims.

I claim:

1. A latch assembly comprising: a movable rack, a pinion, said pinion engaging said rack to drive the same, a keeper housing, a keeper, said keeper comprising a plurality of teeth, said teeth meshed with said rack, said keeper contained within said keeper housing, said keeper positioned on said rack for parallel movement therewith, and a latch, said latch engaging said keeper.

2. The latch assembly of claim 1 further comprising a casement window, said casement window comprising a frame and a pivotable section, said pivotable section hingedly attached to said frame, said movable rack positioned on said frame and said latch affixed to said pivotable section.

3. The latch assembly of claim 1 wherein said keeper housing defines a latch opening.

4. The latch assembly of claim 3 wherein said latch engages said keeper through said latch opening.

5. A latch assembly mounted on a window having a frame and a pivotable section, the pivotable section hingedly joined to the frame, said latch assembly comprising: a first keeper housing mounted on the window frame, a first keeper, said first keeper positioned within said first keeper housing, a movable rack, said first keeper engaging said movable rack for parallel movement therewith, a pinion, a pinion handle, said pinion handle joined to said pinion, said pinion engaging said movable rack to drive the same, said pinion affixed to the window frame, a first latch, said first latch affixed to the window pivotable section whereby upon closing the window pivotable section against the window frame, said pinion can be rotated to move said rack to engage said first latch with said first keeper.

6. The latch assembly of claim 5 further comprising a pawl, said pawl affixed to said pinion handle.

7. The latch assembly of claim 6 further comprising a pinion cover, said pinion contained within said pinion cover.

8. The latch assembly of claim 7 wherein said pinion cover defines a notch, said pawl engageable with said notch.

9. A latch assembly comprising: a movable rack, a pinion, said pinion engaging said rack to drive the same, a keeper housing, a keeper, a keeper arm, said keeper arm affixed to said keeper, a plurality of arm teeth, said arm teeth attached to said keeper arm and engaging said rack for parallel movement of said keeper and said rack, said keeper contained within said keeper housing, and a latch, said latch engaging said keeper.

10. The latch assembly of claim 9 further comprising a casement window, said casement window comprising a frame and a pivotable section, said pivotable section hingedly attached to said frame, said movable rack positioned on said frame and said latch affixed to said pivotable section.

11. The latch assembly of claim 9 wherein said keeper is L-shaped.

12. The latch assembly of claim 9 wherein said keeper housing defines a latch opening.

13. The latch assembly of claim 12 wherein said latch engages said keeper through said latch opening.

14. A latch assembly mounted on a window having a frame and a pivotable section, said pivotable section hingedly joined to the window frame, said latch assembly comprising: a first keeper housing mounted on the window frame, a first keeper, said first keeper positioned within said first keeper housing, a movable rack, said first keeper engaging said movable rack for linear movement therewith, a pinion, a pinion handle, said pinion handle joined to said pinion, said pinion engaging said movable rack to drive the same, said pinion affixed to the window frame, a first latch, said first latch affixed to the window pivotable section whereby upon closing the window pivotable section against the window frame, said pinion can be rotated to move said rack and engage said first latch with said first keeper.

15. The latch assembly of claim 14 further comprising a pawl, said pawl rotatably affixed to said pinion handle.

16. The latch assembly of claim 15 further comprising a pinion cover, said pinion cover defining a notch, said pawl engaging said notch.

17. The latch assembly of claim 16 further comprising a resilient shroud, said shroud positioned on said pinion cover.

18. The latch assembly of claim 14, wherein said movable rack comprises a front rack and a rear rack, said front rack connected to said rear rack, said front rack and said rear rack each defining teeth, said teeth of said front rack positioned opposite of said teeth of said rear rack.

* * * * *